(12) United States Patent
Barrus

(10) Patent No.: US 11,094,397 B2
(45) Date of Patent: Aug. 17, 2021

(54) SECURE COMMUNICATION OF SENSITIVE GENOMIC INFORMATION USING PROBABILISTIC DATA STRUCTURES

(71) Applicant: NOBLIS, INC., Reston, VA (US)

(72) Inventor: Tyler W. Barrus, Midlothian, VA (US)

(73) Assignee: NOBLIS, INC., Reston, VA (US)

( * ) Notice: Subject to any disclaimer, the term of this patent is extended or adjusted under 35 U.S.C. 154(b) by 438 days.

(21) Appl. No.: 15/977,646

(22) Filed: May 11, 2018

(65) Prior Publication Data

US 2018/0330052 A1 Nov. 15, 2018

Related U.S. Application Data

(60) Provisional application No. 62/505,376, filed on May 12, 2017.

(51) Int. Cl.
*G16B 30/00* (2019.01)
*G06N 7/00* (2006.01)
(Continued)

(52) U.S. Cl.
CPC ....... *G16B 30/00* (2019.02); *G06F 16/90344* (2019.01); *G06F 21/602* (2013.01);
(Continued)

(58) Field of Classification Search
CPC ............. G06F 16/90344; G06F 21/602; G06F 21/6254; G16B 30/00; G16B 20/00;
(Continued)

(56) References Cited

U.S. PATENT DOCUMENTS 8,290,972 B1 10/2012 Deshmukh et al.
8,898,204 B1 11/2014 Sathe et al.
(Continued)

OTHER PUBLICATIONS

Bloom, B.H. (Jul. 1970). "Space/Time Trade-offs in Hash Coding with Allowable Errors," Communications of the ACM 13(7): 422-426.
(Continued)

*Primary Examiner* — Robert W Beausoliel, Jr.
*Assistant Examiner* — Susan F Rayyan
(74) *Attorney, Agent, or Firm* — Morrison & Foerster LLP

(57) ABSTRACT

Techniques for securely encoding, communicating, and comparing genomic information using probabilistic data structures are provided. In some embodiments, genomic information in a secure computing environment may be encoded and/or anonymized by building a probabilistic data structure that represents sub-strings of the genomic information as members of a set; the probabilistic data structure may then be securely transmitted outside the secure computing environment. In some embodiments, a probabilistic data structure representing sub-strings of sensitive genomic information as members of a set may be received in an unsecure computing environment and may be queried to generate output data indicating whether reference sub-strings are probable members of the set. In some embodiments, querying the probabilistic data structure, and other techniques of analyzing the probabilistic data structure, may be used to determine whether the sensitive genomic information corresponds to an organism associated with the reference genomic information.

13 Claims, 4 Drawing Sheets

(51) Int. Cl.

| | | |
|---|---|---|
| *G16H 10/60* | (2018.01) | |
| *G06F 21/62* | (2013.01) | |
| *G06F 16/903* | (2019.01) | |
| *G16B 20/00* | (2019.01) | |
| *G16B 40/00* | (2019.01) | |
| *G06F 21/60* | (2013.01) | |
| *G16B 50/40* | (2019.01) | |
| *G16H 10/40* | (2018.01) | |

(52) U.S. Cl.
CPC ......... *G06F 21/6254* (2013.01); *G06N 7/005* (2013.01); *G16B 20/00* (2019.02); *G16B 40/00* (2019.02); *G16B 50/40* (2019.02); *G16H 10/40* (2018.01); *G16H 10/60* (2018.01)

(58) Field of Classification Search
CPC ........ G16B 40/00; G16B 50/40; G06N 7/005; G16H 10/60; G16H 10/40
See application file for complete search history.

(56) References Cited

U.S. PATENT DOCUMENTS

| 9,817,944 | B2* | 11/2017 | Kural ................... G16B 30/00 |
| 10,642,994 | B1 | 5/2020 | Allen et al. |
| 10,790,984 | B1 | 9/2020 | Stiles |
| 2008/0040047 | A1* | 2/2008 | Nelson ................. G16B 30/00 702/20 |
| 2008/0306694 | A1* | 12/2008 | Izmailov ............... G16B 30/00 702/19 |
| 2008/0313132 | A1 | 12/2008 | Hao et al. |
| 2009/0030895 | A1 | 1/2009 | Eswaran et al. |
| 2009/0241187 | A1 | 9/2009 | Troyansky |
| 2011/0098193 | A1* | 4/2011 | Kingsmore .......... C12Q 1/6869 506/9 |
| 2011/0225191 | A1 | 9/2011 | Xie |
| 2013/0244614 | A1 | 9/2013 | Santamaria et al. |
| 2014/0238937 | A1* | 8/2014 | McGinnis ............ B01D 61/005 210/636 |
| 2014/0274752 | A1* | 9/2014 | Blume .................. G16C 20/60 506/8 |
| 2015/0220684 | A1* | 8/2015 | Greenfield ............ G16C 99/00 707/722 |
| 2016/0132640 | A1 | 5/2016 | Layer et al. |
| 2016/0179893 | A1 | 6/2016 | He |
| 2016/0344849 | A1* | 11/2016 | Thomas ............... H03M 7/3093 |
| 2017/0068776 | A1* | 3/2017 | Godinez-Moreno .. G16B 30/00 |
| 2017/0070492 | A1 | 3/2017 | Rubin et al. |
| 2018/0011852 | A1 | 1/2018 | Bennett et al. |
| 2018/0089365 | A1* | 3/2018 | Beal ....................... G16B 35/20 |
| 2018/0248698 | A1 | 8/2018 | Kominar et al. |
| 2018/0330054 | A1 | 11/2018 | Omari et al. |
| 2019/0155835 | A1* | 5/2019 | Daugharthy ............. G06T 7/70 |
| 2019/0236267 | A1 | 8/2019 | Sanders et al. |
| 2019/0318807 | A1* | 10/2019 | O'Hara ................ C12Q 1/6888 |

OTHER PUBLICATIONS

Hellman, M.E (Jul. 1980). "A Cryptanalytic Time-Memory Trade-Off," IEEE Transactions on Information Theory 26(4): 401-406.

Omari et al., U.S. Office Action dated Mar. 3, 2020, directed to U.S. Appl. No. 15/977,667; 19 pages.

Omari et al., Office Action dated Oct. 29, 2020, directed to U.S. Appl. No. 15/977,667; 23 pages.

Sanders et al., Notice of Allowance dated Mar. 10, 2021, directed to U.S. Appl. No. 16/253,950; 18 pages.

\* cited by examiner

200

232
Generate and store second probabilistic data structure representing genomic reference data, wherein the probabilistic data structure represents each of the one or more of the plurality of reference sub-strings as a member of a second set

234
The second probabilistic data structure is a second Bloom filter, wherein each of the one or more of the plurality of sub-strings is an element of the Bloom filter

236
Compare first probabilistic data structure to second probabilistic data structure

238
Based on comparison of first probabilistic data structure and second probabilistic data structure, generate and store index indicative of similarity of first probabilistic data structure and second probabilistic data structure

240
The index is a Jaccard index indicating similarity of the first and second Bloom filters

FIG. 2C

SECURE COMMUNICATION OF SENSITIVE GENOMIC INFORMATION USING PROBABILISTIC DATA STRUCTURES

REFERENCE TO RELATED APPLICATIONS

This application claims the benefit of U.S. Provisional Application No. 62/505,376, entitled, "SECURE COMMUNICATION OF SENSITIVE GENOMIC INFORMATION USING PROBABILISTIC DATA STRUCTURES," filed May 12, 2017, the entire contents of which are incorporated herein by reference.

FIELD OF THE INVENTION

This relates generally to using probabilistic data structures to anonymize data and more specifically to using Bloom filters to anonymize genomic data.

BACKGROUND OF THE INVENTION

Whole genome sequence ("WGS") of an unknown sample can provide a vast amount of information, including sample identification, when compared to a known dataset. However, the amount of knowledge to be gained is only as good as the known dataset against which the sample is compared. While public genomic information databases are available, private organizations have vast troves of additional genomic information associated with rare organisms that is not available in the public domain.

However, many private organizations are hesitant or unwilling to freely and/or fully share private genomic information because the information may be considered sensitive or secure. For example, a private organization may be hesitant to be associated with genomic information of a pathogen that may be associated with past or future illnesses, contaminations, outbreaks, recalls, or the like. Alternately or additionally, genomic information may be considered sensitive or secure because it may be relevant to military applications. Thus, known solutions for performing genomic data analytics either (a) forego the vast amount of genomic information that private organizations are unwilling to disclose or (b) redact, exclude, or obscure so much of the private genomic information that the information that is shared is not valuable for genomic data analytics.

SUMMARY OF THE INVENTION

As described above, known solutions for performing genomic data analytics forego the vast amount of genomic information that private organizations are unwilling to disclose. Thus, there is a need for methods of processing, storing, and transferring genomic information such that the information may be secured and anonymized while still being able to be meaningfully processed and analyzed for genomic data analytics. Disclosed herein are systems, methods, and techniques that address this need by allowing for encoding, compressing, and/or anonymizing genomic information. This may facilitate allowing the information to be safely disclosed and securely analyzed after encoding and anonymization. The systems, methods, and techniques disclosed herein may thus allow genomic information analytics to be applied to the large amounts of private genomic information without placing the parties associated with the genomic information at undue risk.

In some embodiments, genomic information may be encoded, anonymized, and/or compressed through the use of one or more probabilistic data structures. In the systems, methods, and techniques disclosed herein, a probabilistic data structure may be used to perform a one-way encoding of genomic data, such that the data may be anonymized before being shared with the public and such that the encoded and anonymized data may still be subject to analysis. The encoded and anonymized information may then be stored in a database of genomic encoded/anonymized/compressed information, and that database may be used for comparisons to reference data and for other genomic analytics. As explained herein, using probabilistic data structures in this way may allow for rapid insertion and lookup of data while maintaining a 0% false negative return rate.

In some embodiments, a probabilistic data structure used for encoding and anonymizing genomic information may be a Bloom filter. A Bloom filter is a probabilistic data structure that may be used to determine whether an element is a member of a set. When a Bloom filter is queried as to whether an element is a member of a set, the Bloom filter will provide zero false negative results but may provide false positive results. Thus, a Bloom filter may be used to determine whether an element is "probably present" or "definitely not present" in a set. The rate at which false positive results are returned may be selected by a user at the time of the creation of a Bloom filter, such that a Bloom filter may be configured to have a predetermined probability of returning false positive results. The false positive rate of a Bloom filter is pre-defined with a correlation to the number of elements to be added to the filter. For example, a Bloom filter may be configured to return false positive results 40%, 30%, 20%, 10%, 5%, 2%, 1%, or less than 1% of the time.

Bloom filters are space-efficient, in that they require less disk space for storage and memory for comparison processes than error-free (e.g., 0% false-positive) hashing techniques or other data structures for representing and searching sets (e.g., search trees, hash tables, arrays, and linked lists). In some embodiments, a Bloom filter having a 1% false positive probability may require less than 10 bits per element represented by the Bloom filter. The lower a false-positive probability is set, the larger the Bloom filter data structure will be; the higher the false-positive probability, the smaller the Bloom filter data structure will be.

In some embodiments, whole genome sequencing data ("WGS data") may be encoded and anonymized by k-merizing the read set and inserting the individual k-mers into a pre-assembled probabilistic data structure. Algorithmically, determining to use either the k-mer or its reverse complement may then reduce the number of elements that are to be tracked and may standardize what will information will be added to the probabilistic data structure. Once inserted into the probabilistic data structure, the data may be effectively irretrievable back into its original form. Once the data is encoded by the techniques described herein into the probabilistic data structure, the data structure may then be used to determine whether an organism is likely included in the set represented by the probabilistic data structure (or whether the organism is definitely not included in the data set represented by the probabilistic data structure). This may be done by comparing the probabilistic data structure to reference genome data of the organism as explained herein.

As explained herein, comparing reference genome data to a probabilistic data structure may allow determination of how similar two anonymized, encoded probabilistic data structures are to one another. For example, comparison of two Bloom filters may allow calculation of a Jaccard Index representative of the comparison. In some embodiments, Bloom filter pairs resulting in a Jaccard index close to one may indicate that the contents of the filters are closely related to one another, containing many of the same k-mers and possibly representing the same species and/or same organism. Conversely, a Bloom filter pair resulting in a Jaccard Index close to zero may indicate that the sequences are not closely related, representing different organisms and/or different species.

In some embodiments, a first system for securely communicating genomic information from a secure computing environment to an unsecure computing environment is provided, the system comprising: one or more processors located in the secure computing environment; a memory located in the secure computing environment, the memory storing one or more programs, the one or more programs configured to be executed by the one or more processors and including instructions to: receive data representing a nucleic acid sequence; divide the data into a plurality of portions, wherein each of the plurality of portions represents a sub-string of the nucleic acid sequence; store data, in the secure computing environment, representing one or more of the plurality of portions; encode the data representing the nucleic acid sequence by generating, based on the data representing one or more of the plurality of portions, data including a probabilistic data structure that represents each of the one or more of the plurality of portions as members of a set; transmit the encoded nucleic acid sequence, including the probabilistic data structure, for storage in the unsecure computing environment, in association with metadata corresponding to the data representing the nucleic acid sequence.

In some embodiments of the first system, the probabilistic data structure is configured to be queried by an element, and to responsively generate data indicating whether the element is a member of the set.

In some embodiments of the first system, generating data indicating whether the element is a member of the set comprises one of generating data indicating that the element is definitely not a member of the set and generating data indicating that the element is probably a member of the set.

In some embodiments of the first system, generating the probabilistic data structure comprises setting a predefined false-positive probability of the probabilistic data structure.

In some embodiments of the first system, the predefined false-positive probability is set at least in part in accordance with a target file size for the probabilistic data structure.

In some embodiments of the first system, the predefined false-positive probability is set at least in part in accordance with available storage resources.

In some embodiments of the first system, the predefined false-positive probability is set at least in part in accordance with available processing resources.

In some embodiments of the first system, the predefined false-positive probability is set at least in part in accordance with requirements for accuracy of comparisons to be made against the probabilistic data structure.

In some embodiments of the first system, the predefined false-positive probability is set at least in part in accordance with a level of sensitivity of the data representing a nucleic acid sequence.

In some embodiments, first method for storing one or more programs for securely communicating genomic information from a secure computing environment to an unsecure computing environment is provided, the first method comprising: at a system comprising one or more processors located in the secure computing environment and a memory located in the secure computing environment: receiving data representing a nucleic acid sequence; dividing the data into a plurality of portions, wherein each of the plurality of portions represents a sub-string of the nucleic acid sequence; storing data, in the secure computing environment, representing one or more of the plurality of portions; encoding the data representing the nucleic acid sequence by generating, based on the data representing one or more of the plurality of portions, data including a probabilistic data structure that represents each of the one or more of the plurality of portions as members of a set; transmitting the encoded nucleic acid sequence, including the probabilistic data structure, for storage in the unsecure computing environment, in association with metadata corresponding to the data representing the nucleic acid sequence.

In some embodiments, a first non-transitory computer-readable storage medium storing one or more programs for securely communicating genomic information from a secure computing environment to an unsecure computing environment is provided, the one or more programs configured to be executed by one or more processors located in the secure computing environment, the one or more programs including instructions to: receive data representing a nucleic acid sequence; divide the data into a plurality of portions, wherein each of the plurality of portions represents a sub-string of the nucleic acid sequence; store data, in the secure computing environment, representing one or more of the plurality of portions; encode the data representing the nucleic acid sequence by generating, based on the data representing one or more of the plurality of portions, data including a probabilistic data structure that represents each of the one or more of the plurality of portions as members of a set; transmit the encoded nucleic acid sequence, including the probabilistic data structure, for storage in the unsecure computing environment, in association with metadata corresponding to the data representing the nucleic acid sequence.

In some embodiments, a second system for securely comparing genomic information in an unsecure computing environment, the second system comprising: one or more processors located in the unsecure computing environment; a memory located in the unsecure computing environment, the memory storing one or more programs, the one or more programs configured to be executed by the one or more processors and including instructions to: receive, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence; receive, from the first source, first metadata associating the encoded data with the first source; receive, from a second source, data representing a reference nucleic acid sequence and associated second metadata that identifies an organism associated with the reference nucleic acid sequence; extract, from the data representing the reference nucleic acid sequence, a plurality of sub-strings each representing a portion of the reference nucleic acid sequence; query the probabilistic data structure by each of the plurality of sub-strings extracted from the reference nucleic acid sequence; generate, in response to the querying, result data comprising one or more indications of whether each of the plurality of sub-strings extracted from the reference nucleic acid sequence is a member of the set of sub-strings of the first nucleic acid sequence; store the result data in association with one or more of the first and second metadata.

In some embodiments of the second system, the one or more programs include instructions to determine, based on the result data, whether the first nucleic acid sequence corresponds to the organism associated with the reference nucleic acid sequence.

In some embodiments of the second system, the determining comprises determining, when more than a predefined threshold of the plurality of sub-strings extracted from the reference nucleic acid sequence are indicated by the result data as being members of the set of sub-strings of the first nucleic acid sequence, that the first nucleic acid sequence corresponds to the organism associated with the reference nucleic acid sequence.

In some embodiments, a second method for securely comparing genomic information in an unsecure computing environment is provided, the second method comprising: at a system comprising one or more processors located in the unsecure computing environment and a memory located in the unsecure computing environment: receiving, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence; receiving, from the first source, first metadata associating the encoded data with the first source; receiving, from a second source, data representing a reference nucleic acid sequence and associated second metadata that identifies an organism associated with the reference nucleic acid sequence; extracting, from the data representing the reference nucleic acid sequence, a plurality of sub-strings each representing a portion of the reference nucleic acid sequence; querying the probabilistic data structure by each of the plurality of sub-strings extracted from the reference nucleic acid sequence; generating, in response to the querying, result data comprising one or more indications of whether each of the plurality of sub-strings extracted from the reference nucleic acid sequence is a member of the set of sub-strings of the first nucleic acid sequence; storing the result data in association with one or more of the first and second metadata.

In some embodiments, a second non-transitory computer-readable storage medium storing one or more programs for securely comparing genomic information in an unsecure computing environment is provided, the one or more programs configured to be executed by one or more processors and including instructions to: receive, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence; receive, from the first source, first metadata associating the encoded data with the first source; receive, from a second source, data representing a reference nucleic acid sequence and associated second metadata that identifies an organism associated with the reference nucleic acid sequence; extract, from the data representing the reference nucleic acid sequence, a plurality of sub-strings each representing a portion of the reference nucleic acid sequence; query the probabilistic data structure by each of the plurality of sub-strings extracted from the reference nucleic acid sequence; generate, in response to the querying, result data comprising one or more indications of whether each of the plurality of sub-strings extracted from the reference nucleic acid sequence is a member of the set of sub-strings of the first nucleic acid sequence; store the result data in association with one or more of the first and second metadata.

In some embodiments, a third system for comparing genomic information is provided, the third system comprising: one or more processors; a memory, the memory storing one or more programs, the one or more programs configured to be executed by the one or more processors and including instructions to: receive a first probabilistic data structure that represents each of a plurality of sub-strings as members of a first set, wherein each of the plurality of sub-strings represents a portion of a first nucleic acid sequence; receive a second probabilistic data structure that represents each of a plurality of sub-strings as members of a second set, wherein each of the plurality of sub-strings represents a portion of a second nucleic acid sequence; compare the first probabilistic data structure and the second probabilistic data structure to generate data indicative of a similarity of the two data structures; store the data indicative of the similarity of the two probabilistic data structures in association with metadata associated with the first and second probabilistic data structures.

In some embodiments of the third system, the one or more programs include instructions to determine, based on the data indicative of the similarity of the two probabilistic data structures, whether the first nucleic acid sequence corresponds to the second nucleic acid sequence.

In some embodiments of the third system, determining whether the first nucleic acid sequence corresponds to the second nucleic acid sequence comprises determining one or more of: whether the first nucleic acid sequence and the second nucleic acid sequence represent the same species, whether the first nucleic acid sequence and the second nucleic acid sequence represent the same organism, whether the first nucleic acid sequence and the second nucleic acid sequence represent the same strain.

In some embodiments of the third system, determining whether the first nucleic acid sequence corresponds to the second nucleic acid sequence comprises determining whether a value included in the data indicative of the similarity of the two probabilistic data structures exceeds a predetermined threshold.

In some embodiments of the third system, the first and second probabilistic data structures are Bloom filters and the data indicative of the similarity of the two probabilistic data structures is a Jaccard index.

In some embodiments, a third method for comparing genomic information is provided, the third method comprising: at a system comprising one or more processors and a memory: receiving a first probabilistic data structure that represents each of a plurality of sub-strings as members of a first set, wherein each of the plurality of sub-strings represents a portion of a first nucleic acid sequence; receiving a second probabilistic data structure that represents each of a plurality of sub-strings as members of a second set, wherein each of the plurality of sub-strings represents a portion of a second nucleic acid sequence; comparing the first probabilistic data structure and the second probabilistic data structure to generate data indicative of a similarity of the two data structures; storing the data indicative of the similarity of the two probabilistic data structures in association with metadata associated with the first and second probabilistic data structures.

In some embodiments, a third non-transitory computer-readable storage medium storing one or more programs for comparing genomic information is provided, the one or more programs configured to be executed by one or more processors and including instructions to: receive a first probabilistic data structure that represents each of a plurality of sub-strings as members of a first set, wherein each of the plurality of sub-strings represents a portion of a first nucleic acid sequence; receive a second probabilistic data structure that represents each of a plurality of sub-strings as members of a second set, wherein each of the plurality of sub-strings represents a portion of a second nucleic acid sequence; compare the first probabilistic data structure and the second probabilistic data structure to generate data indicative of a similarity of the two data structures; store the data indicative of the similarity of the two probabilistic data structures in association with metadata associated with the first and second probabilistic data structures.

Any of the features of any of the embodiments listed above or elsewhere herein may be combined with one another.

BRIEF DESCRIPTION OF THE DRAWINGS

FIGS. 2A-2C show a flow diagram depicting a method for encoding genomic information in accordance with some embodiments.

DETAILED DESCRIPTION OF THE INVENTION

The following description sets forth exemplary methods, parameters, and the like. It should be recognized, however, that such description is not intended as a limitation on the scope of the present disclosure but is instead provided as a description of exemplary embodiments.

Traditional techniques for bioinformatics and genomic data analytics require the disclosure of private genomic information in order for meaningful comparisons of that private information to be made against other private genomic information or against publicly available reference genomic information. For example, in order for a database of genomic information such as food pathogens to be built and expanded, private organizations would be required to disclose genomic information associated with their organizations. Due to the sensitive nature of certain private genomic information, many organizations have been reluctant or unwilling to disclose said private genomic information. Thus, bioinformatics systems have been required to operate without access to vast troves of private genomic information, making bioinformatics applications less effective due to the inability to compile robust and ever-expanding databases of the most recent genomic information from various public and private sources.

Accordingly, there is a need for systems, methods, and techniques for securely disclosing sensitive private genomic information for storage and/or application in bioinformatics databases. Disclosed herein are systems, methods, and techniques that address this need by allowing for encoding, compressing, and/or anonymizing genomic information such that the information may be safely disclosed and securely analyzed. The systems, methods, and techniques disclosed herein may thus allow genomic information analytics to be applied to the large amounts of private genomic information without placing the parties associated with the genomic information at undue risk.

Below, FIGS. 1 and 2A-2C provide a description of exemplary systems and methods for performing the techniques for securely disclosing sensitive private genomic information for storage and/or application in bioinformatics databases, as disclosed herein.

Figure 1:
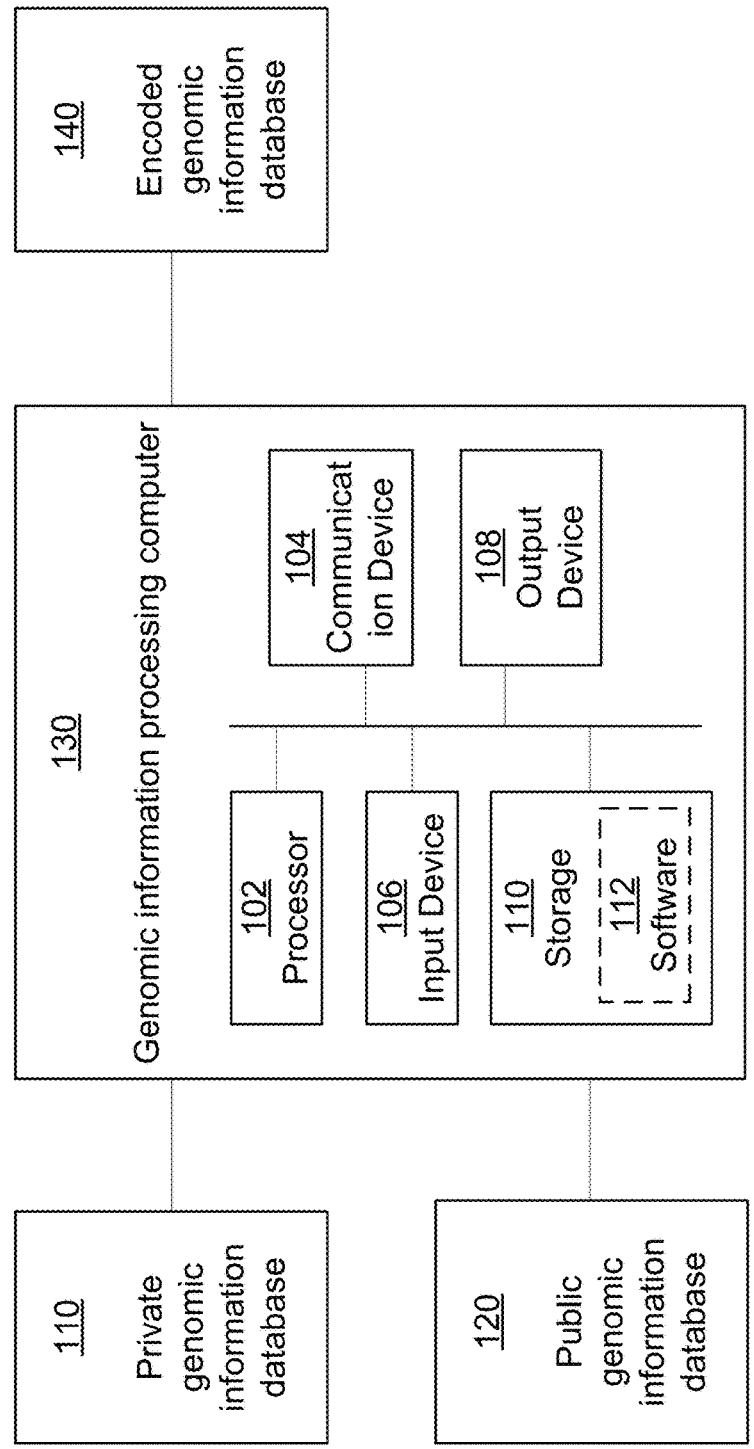
FIG. 1 shows a bioinformatics system in accordance with some embodiments.

FIG. 1 depicts a bioinformatics system 100, in accordance with some embodiments, that is configured to perform one or more software processes that, when executed, provide one or more aspects of the disclosed embodiments. FIG. 1 is not intended to be limiting to the disclosed embodiment as the components used to implement the processes and features disclosed herein may vary.

As shown in FIG. 1, in some embodiments, system 100 may comprise one or more private genomic information databases, one or more public genomic information databases, one or more genomic information processing computers, and one or more encoded genomic information databases. System 100 may be configured to process genomic information and associated metadata received from public and/or private genomic information databases and to store the processed (e.g., encoded, compressed, anonymized, etc.) data in one or more encoded genomic information databases. As explained herein, processing and storing the genomic information in such a manner may allow for more secure, fast, efficient, and accurate analytics of the genomic information.

In some embodiments, system 100 comprises private genomic information database 110. Private genomic information database 110 may be any computer system or server system associated with any private entity, storing genomic information associated with one or more organisms and/or samples. In some embodiments, private genomic information database 110 may be associated with a one or more corporations, educational institutions, laboratories, government entities, medical facilities, military facilities, packaging facilities, processing facilities, factories, distribution facilities, shipping terminals, warehouses, transportation hubs, stores, markets, restaurants, farms, ranches, slaughterhouses, or the like. Private genomic information database 110 may store genomic information in any human-readable and/or machine-readable format, such as .fasta file format, .fastq file format, general feature format (GFF), and/or .SRA file format.

In some embodiments, the genomic information and/or genomic data stored on private genomic information database 110, like genomic information and/or genomic data references elsewhere herein, may be data representing one or more nucleic acid sequences.

In some embodiments, private genomic information database 110 may store private genomic information associated with one or more organisms and/or samples along with metadata. In some embodiments, metadata may include data relating to an identity of an organism associated with a sample; one or more associated parties or organizations; one or more data sources; location information and/or time information at which a sample was taken; a type of a sample; a manner in which a sample was collected; a party that collected a sample; a manner in which (and parties by which) a sample was transported; locations and/or routes along which a sample was transported, including times at which the sample was present at various locations; confidentiality metadata indicating a confidentiality level of a sample and/or of an associated party; genomic information that is known or suspected about a sample before sequencing and/or before post-sequencing bioinformatics processing, such as a known or suspected organism, known or suspected serovar, or other known or suspected genomic information; a time at which a sample was located at one or more facilities or locations; personnel that came into contact with a sample at various times; and/or a transportation service associated with a sample. In some embodiments, some or all metadata may be fully or partially anonymized before or after receipt by system 100.

In some embodiments, system 100 may comprise public genomic information database 120. Public genomic information database 120 may be any computer system or server system that is publicly and/or widely accessible via public or private electronic communication networks, storing genomic information associated with one or more organisms and/or samples. In some embodiments, genomic information database 110 may store genomic information in any human-readable and/or machine-readable format, such as .fasta file format, .fastq file format, general feature format (GFF), and/or .SRA file format.

In some embodiments, public genomic information database 120 may store WGS reference data (e.g., reference genomes) for one or more known organisms and may be accessible via the internet. For example, public genomic information database may include or be related to the National Center for Biotechnology Information (NCBI) database, the European Molecular Biology Laboratory (EMBL) database, and/or the DNA Database of Japan (DDBJ).

In some embodiments, system 100 may comprise genomic information processing computer 130, which may be any computer configured to receive, process, analyze, and store genomic data as described further herein. Genomic information processing computer 130 can be any suitable type of microprocessor-based device, such as a personal computer; workstation; server; handheld computing device, such as a phone or tablet; or distributed computing system (e.g., cloud computing system). The system can include, for example, one or more of processor 102, communication device 104, input device 106, output device 108, storage 110, and/or software 112 stored on storage 110 and executable by processor 102. The components of the computer can be connected in any suitable manner, such as via one or more physical buses or wirelessly.

In some embodiments, genomic information processing computer 130 may include server-side computing components as well as client-side computing components. The specific elements shown in FIG. 1 may, in some embodiments, be included in a server-side computer and/or may, in some embodiments, be included in a client-side computer. In some embodiments, genomic information processing computer 130 may include server-side components and client-side components that are in communication with one another via one or more instances of communication device 104, which may, for example, enable communication of server-side components and client-side components over a network connection.

In some embodiments, some or all components of genomic information processing computer 130 may be part of a distributed computing system (e.g., a cloud computing system). In some embodiments of the techniques disclosed herein, for example, storage 110 may be storage provisioned by a cloud computing system, such that a user may send instructions to the cloud computing system over one or more network connections, and the cloud computing system may execute the instructions in order to leverage the cloud computing components in accordance with the instructions. In some embodiments, cloud computing systems may be configured to be capable of executing the same or similar program code in the same programming languages as other systems (e.g., servers, personal computers, laptops, etc.) as discussed herein.

Processor 102 may be any suitable type of computer processor capable of communicating with the other components of genomic information processing computer 130 in order to execute computer-readable instructions and to cause genomic information processing computer 130 to carry out actions in accordance with the instructions. For example, processor 100 may access a computer program (e.g., software 112) that may be stored on storage 110 and execute the program to cause the system to perform various actions in accordance with the program. In some embodiments, a computer program or other instructions executed by processor 102 may be stored on any transitory or non-transitory computer-readable storage medium readable by processor 102.

In some embodiments, processor 102 may include one or more known processing devices, such as a microprocessor from the Pentium™ family manufactured by Intel™ or the Turion™ family manufactured by AMD™. Processor 102 may include a single core or multiple core processor system that provides the ability to perform parallel processes simultaneously. For example, processing unit 111a may include a single core processor that is configured with virtual processing technologies known to those skilled in the art. In certain embodiments, processor 102 may use logical processors to simultaneously execute and control multiple processes. The one or more processors in processor 102 may implement virtual machine technologies, or other similar known technologies, to provide the ability to execute, control, run, manipulate, store, etc., multiple software processes, applications, programs, etc. In another embodiment, processor 102 may include a multiple-core processor arrangement (e.g., dual or quad core) that is configured to provide parallel processing functionalities to allow genomic information processing computer 130 to execute multiple processes simultaneously. Other types of processor arrangements, such as those used in Cray supercomputers, could be implemented to provide for the capabilities disclosed herein.

Communication device 104 may include any suitable device capable of transmitting and receiving signals over a network, such as a network interface chip or card. Genomic information processing computer 130 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Input device 106 may be any suitable device that provides input, such as a touchscreen or monitor, keyboard, mouse, button or key or other actuatable input mechanism, microphone, and/or voice-recognition device, gyroscope, camera, or IR sensor. Output device 108 may be any suitable device that provides output, such as a touchscreen, monitor, printer, disk drive, light, speaker, or haptic output device. Input device 106 and/or output device 108 may include components configured to send and/or receive information between components of genomic information processing computer 130 or external to genomic information processing computer 130.

Storage 110 can be any suitable device the provides storage, such as an electrical, magnetic or optical memory including a RAM, cache, hard drive, CD-ROM drive, tape drive, or removable storage disk. In some embodiments, storage 110 may include instructions that, when executed by one or more processors of processor 102, perform one or more processes consistent with the functionalities disclosed herein. Storage 110 may also include any combination of one or more databases controlled by memory controller devices (e.g., server(s), etc.) or software, such as document management systems, Microsoft SQL databases, SharePoint databases, Oracle™ databases, Sybase™ databases, or other relational databases. In some embodiments, storage 110 may contain or be communicatively coupled to any one or more of the databases discussed herein.

In some embodiments, instructions, application programs, etc., may be stored in an external storage or available from a memory over a public or private network to which genomic information processing computer 130 is communicatively coupled. The one or more processors in processor 102 may execute one or more programs located remotely from genomic information processing computer 130 and/or system 100. For example, genomic information processing computer 130 may access one or more remote programs, that, when executed, perform functions related to disclosed embodiments. Storage 110 may include one or more memory devices that store data and instructions used to perform one or more features of the disclosed embodiments.

Software 112, which may be stored in storage 110 and executed by processor 102, may include, for example, the programming that embodies the functionality of the methods, techniques, and other aspects of the present disclosure (e.g., as embodied in the computers, servers, and devices as described above). In some embodiments, software 112 may include a combination of servers, such as application servers and database servers.

Methods, systems, and articles of manufacture consistent with disclosed embodiments are not limited to separate programs or computers configured to perform dedicated tasks. For example, genomic information processing computer 130 may include storage that may include one or more programs to perform one or more functions for encoding, compressing, and/or anonymizing genomic information by way of probabilistic data structures and/or performing comparisons or other analytics on the probabilistic data structures.

Software 112 can also be stored and/or transported within any computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 110, that can contain or store programming for use by or in connection with an instruction execution system, apparatus, or device.

Software 112 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport readable medium can include, but is not limited to, an electronic, magnetic, optical, electromagnetic, or infrared wired or wireless propagation medium.

Genomic information processing computer 130 can implement any one or more operating systems suitable for operating on the network. Software 112 can be written in any one or more suitable programming languages, such as C, C++, Java, or Python. In various embodiments, application software embodying the functionality of the present disclosure can be deployed in different configurations, such as in a client/server arrangement or through a Web browser as a Web-based application or Web service, for example.

In some embodiments, one or both of private genomic information database 110 and public genomic information database 120 may be communicatively coupled by a public or private electronic communication network with genomic information processing computer 130. Genomic information processing computer 130 may be communicatively connected to one or more memory devices (e.g., databases (including but not limited to private database 112 and public database 114)) locally or through a public or private network. The remote memory devices may be configured to store information and may be accessed and/or managed by genomic information processing computer 130. By way of example, the remote memory devices may be document management systems, Microsoft SQL databases, SharePoint databases, Oracle™ databases, Sybase™ databases, or other relational databases. Systems and methods of disclosed embodiments, however, are not limited to separate databases or even to the use of a database.

In some embodiments, genomic information processing computer 130 may create, receive, store, and/or provide one or more indexes of a nucleic acid sequence or an amino acid sequence. Any such index may include a plurality of elements, with each element corresponding to a permutation of a nucleic acid sequence or an amino acid sequence (or another type of sequence). Genomic information processing computer 130 may implement the index using a variety of data structures, such as databases, matrices, arrays, linked lists, trees, and the like. The choice of data structures may vary. Genomic information processing computer 130 may store the index in storage 110 and/or in one or more associated databases. More specifically, the index may be stored on hard disk; genomic information processing computer 130 may also load the index into RAM for increased performance.

In some embodiments, genomic information processing computer 130 may create, receive, store, and/or provide one or more probabilistic data structures. Any such probabilistic data structures may include, represent, or correspond to one or more elements included in a data set. In some embodiments, any such probabilistic data structure may be created based on genomic information, wherein one or more strings, substrings, or other characteristics of genomic information and/or associated metadata may be an element represented as part of a set by a probabilistic data structure. Genomic information processing computer 130 may store the probabilistic data structure in storage 110 and/or in one or more associated databases. More specifically, the probabilistic data structure may be stored on hard disk; genomic information processing computer 130 may also load the probabilistic data structure into RAM for increased performance.

In some embodiments, system 100 may comprise encoded genomic information database 140. Encoded genomic information database 140 may be any computer system or server system configured to store encoded, compressed, and/or anonymized genomic information, and in some embodiments configured to store other genomic information (e.g., non-encoded, non-compressed, and/or non-anonymized genomic information) as well as metadata. Like private genomic information database 110 and public genomic information database 120, encoded genomic information database 140 may be communicatively coupled to genomic information processing computer 130.

As explained further below, genomic information processing computer 130 may be configured to encode, compress, and/or anonymize genomic information from private genomic information database 110 and/or public genomic information database 120, such as by creating one or more probabilistic data structures based on the genomic information. In some embodiments, the encoded, compressed, and/or anonymized genomic information may be stored on encoded genomic information database 140 for future access and/or reference by one or more parties or organizations, including for use in bioinformatics and genomic analytics processes.

In some embodiments, encoded genomic information database 140 may be widely or publicly available, such as being accessible via the internet. In some embodiments, encoded genomic information database 140 may be accessible only by verified or approved parties; encoded genomic information database 140 may be accessible by a larger group of people and/or entities than have access to private genomic information database 110 but may be accessible by a smaller group of people and/or entities than have access to public genomic information database 120. In some embodiments, encoded genomic information database 140 may be accessible by subscribers to a bioinformatics system and/or service.

In some embodiments, encoded genomic information database 140 may store genomic information in any human-readable and/or machine-readable format, such as any of the file formats discussed above with respect to either private genomic information database 110 or public genomic information database 120. In some embodiments, the genomic information stored in encoded genomic information database 140 may be in a format configured to be applied to an index, for example as described in U.S. patent application Ser. No. 15/337,754, titled "Food Pathogen Bioinformatics," which is hereby incorporated by reference in its entirety. In some embodiments, the information stored in encoded genomic information database 140 may be compressed information, such as any of the compressed information described in U.S. patent application Ser. No. 14/718,950, titled "Compression and Transmission of Genomic Information," which is hereby incorporated by reference in its entirety. In some embodiments, private database 112 may include a stored generalized index such that compressed genomic information may be applied against the database's stored generalized index to be decompressed, such as described in U.S. patent application Ser. No. 14/718,950, as may be required.

As explained in detail below, encoded genomic information database 140 may store genomic information as one or more probabilistic data structures, such as one or more Bloom filters, which may be used to quickly and efficiently perform comparisons between private read-set data and public reference genomic data (e.g., WGS data) to identify or classify the read-set data without exposing parties associated with the un-encoded genomic information to unnecessary risk of exposure or undeniable association with the genomic information.

FIG. 2 depicts a method for processing, storing, and analyzing genomic information via probabilistic data structures, in accordance with some embodiments. The method 200 may be performed by a system such as the system 100 described above with reference to FIG. 1. In the described embodiments, certain method steps are performed by certain parties or by certain system components; however, in other embodiments, each of the method steps may be performed by any of the other parties described herein, or the parties performing each step may be associated with one another, or may be a related party, or may be the same party.

As will be described below, the methods described herein, including exemplary method 200, may enable secure, fast, efficient, accurate, and precise transfer, storage, and analysis of sensitive genomic information without exposing parties associated with the genomic information to unnecessary risk of being proven to be associated with the genomic information. The methods may further allow for rapid and effective analysis of encoded genomic information and may further allow for efficient and compact transmission and storage of encoded genomic information, requiring less storage and processing resources than known methods.

At block 202, in some embodiments, sensitive genomic data may be received. In some embodiments, the sensitive genomic data may be data representing one or more nucleic acid sequences. In some embodiments, sensitive genomic data may be received by one or more computers configured to store, analyze, process, encode, and/or transmit the sensitive genomic data. In the example of system 100 of FIG. 1, sensitive genomic data may be received by genomic information processing computer 130 from private genomic information database 110.

In some embodiments, the sensitive genomic data received may be any genomic data that is accessible by one or more parties or entities but not widely available to a larger body or to the general public. For example, sensitive genomic data may be any data, as discussed above, stored in a private genomic information database such as private genomic information database 110. In some embodiments, sensitive genomic data may be considered to be sensitive by nature of being private data inaccessible to the general public, by nature of having one or more actual or potential military applications, by nature of being associated with one or more known illnesses and/or outbreaks, and/or by nature of being potentially associated with one or more future illnesses and/or outbreaks.

In some embodiments, the sensitive genomic data may be read-set data pertaining to one or more samples and/or organisms; in some embodiments, the sensitive genomic data may be sequenced data and/or WGS data. In some embodiments, the sensitive genomic data may be received in association with metadata, such as any of the metadata discussed above with respect to private genomic information database 110 in FIG. 1.

At block 204, in some embodiments, genomic reference data may be received. In some embodiments, the genomic reference data may be data representing one or more nucleic acid sequences. In some embodiments, genomic reference data may be received by one or more computers configured to store, analyze, process, encode, and/or transmit the genomic reference data. In the example of system 100 of FIG. 1, sensitive genomic data may be received by genomic information processing computer 130 from public genomic information database 120. In some embodiments, the genomic reference data may include WGS data identified as being associated with a specific organism and may be stored along with metadata identifying the reference data as the specific organism (e.g., a specific genus, species, strain, serovar, etc.). In some embodiments, the genomic reference data may be received in association with metadata, including metadata identifying an organism represented by the genomic reference data and/or including any of the metadata discussed above with respect to private genomic information database 110 in FIG. 1.

In some embodiments, block 206 may follow from block 202 and/or block 204.

At block 206, in some embodiments, the sensitive genomic data and the genomic reference data may be divided into a plurality of sub-strings. The sub-strings resulting from the sensitive genomic data may be referred to as sensitive sub-strings, while the sub-strings resulting from the genomic reference data may be referred to as reference sub-strings.

In some embodiments, blocks 206-216, which may apply to both the sensitive genomic data and to the reference genomic data, may be applied to each type of data at one time, at different times, at one location (e.g., the same computer) or at different locations. In the example of system 100 in FIG. 1, block 206 may be performed by the genomic information processing computer 130 with respect to both the sensitive genomic data and the reference genomic data; however, in some embodiments, different computers may be used for each of the different types of data. For example, in some embodiments, genomic reference data may be processed by a central computer of a public or multi-party organization, while sensitive genomic data may be processed by a computer of a private organization associated with the sensitive genomic data; in this way, only encoded genomic data, and not raw genomic data, may be transmitted from the private organization to outside parties or entities. In some embodiments, blocks 206-216 may be performed concurrently with respect to both the sensitive genomic data and the reference genomic data, while in some embodiments the different data types may be individually subject to blocks 206-216 at different times.

Regardless of the location at which block 206 is carried out, block 206 may involve dividing a string or sequence of genomic data into a plurality of sub-strings having a shorter length than the original string of genomic data.

At block 208, in some embodiments, the sensitive sub-strings and reference sub-strings may be of predetermined length k, where k is the number of bases in the sub-string. At block 210, in some embodiments, the sensitive genomic data and the genomic reference data may be respectively divided into respective pluralities of sub-strings, wherein each plurality of sub-strings numbers (L−k+1), where L is the number of bases in the original string of the respective genomic data.

In some embodiments, this process of dividing a string of genomic data into a plurality of sub-strings may be referred to as "k-merizing" the string of genomic data, in that each of the sub-strings into which the string is divided may be referred to as a k-mer. In some embodiments, the specific number to which k is set may be used to refer to the k-mer; for example, if k is equal to 16, then the k-mer may be referred to as a 16-mer, and if k is equal to 12, then the k-mer may be referred to as a 12-mer. By selecting a predetermined length k, and dividing an overall string of genomic information into sub-strings of length k by shifting down the string by one base per iteration, the overall string may be k-merized into (L−k+1) sub-strings or k-mers of length k.

In some embodiments, the k-merization process may be applied to one or more strings of genomic information from the sensitive genomic data (e.g., a read-set) and also to one or more strings of genomic information from the genomic reference data (e.g., WGS data). In some embodiments, the length k used for the k-merization of both types of data may be the same, such that the sensitive sub-strings and the reference sub-strings may have the same length. In some embodiments, by k-merizing the sensitive genomic data and the genomic reference data using the same length k, different numbers of k-mers may be generated for the sensitive genomic data and the genomic reference data. For example, if a WGS data corresponding to the genomic reference data has a longer length L than a read-set of the sensitive genomic data, then more reference sub-strings may be generated than sensitive sub-strings. In some embodiments, such as where L is equivalent in the sensitive genomic data and the genomic reference data, the number of sub-strings of each type may be the same.

At block 212, in some embodiments, data representing one or more of the plurality of sensitive sub-strings and one or more of the plurality of reference sub-strings may be stored. In some embodiments, the data representing one or more of the plurality of sub-strings may be stored or represented using a hashmap in association with WGS data and/or .fasta or .fastq file formats. In some embodiments, all of those reference sub-strings and all of the sensitive sub-strings may be stored in a database and/or other computer storage or memory associated with the system. In the example of system 100 of FIG. 1, the one or more of the plurality of sub-strings may be transmitted from genomic information processing computer 130 to encoded genomic information database 140 for storage. In some embodiments, the one or more sub-strings may be stored along with metadata, such as metadata identifying the genomic information (e.g., the overall string) to which the sub-string corresponds, and/or metadata identifying a source, organism, and/or sample associated with the genomic information. Thus, by storing the sub-strings along with metadata identifying source information, a system and/or user may be able to look up individual sub-strings to determine which sub-strings correspond to which original genomic information.

In some embodiments, metadata indicating a location in the original string of genomic data may be stored in association with one or more of the sub-strings, while in some embodiments no such location data may be stored.

At block 214, in some embodiments, storing data representing one or more of the plurality of sensitive sub-strings and one or more of the plurality of reference sub-strings may comprise storing data representing only unique sensitive sub-strings or unique reference sub-strings. For example, a system may only store data once for each sub-string that is determined to appear in genomic data, instead of storing multiple data elements in the event that the same sub-string appears two or more times in different locations in the same original string of genetic data. For example, in embodiments in which the sub-strings themselves are stored, a system may store only one copy of each unique sub-string, rather than storing multiple copies of sub-strings that appear more than once. Thus, rather than storing an exhaustive list of each k-mer of length k that appears at each and every position of the genetic data, a system may instead compile a list or stored record that comprises or represents all unique k-mers that appear in the genetic data. In some embodiments, this record of unique k-mers may be stored as a list of each unique k-mer, as a plurality of pointers to an index in which each unique k-mer may be looked up, or in any other suitable format. By storing only data corresponding to unique k-mers and not to each and every k-mer appearing in genetic data, computational and storage resources may both be conserved, while the look-up functions discussed further below may not be compromised.

In some embodiments, despite only storing unique sub-strings or only storing one record of each unique sub-string, an associated record or other indication may also be stored indicating how many times each unique sub-string is encountered in the data.

At block 216, in some embodiments, storing data representing one or more of the plurality of sensitive sub-strings and one or more of the plurality of reference sub-strings may comprise generating and storing data corresponding to a reverse compliment of one or more of the sub-strings. Because sequenced genomic data corresponding to the same portion of the same genome of the same organism may be sequenced either as a first sequence of bases or as the reverse complement (e.g., a reverse complement of a sequence of DNA is formed by interchanging A and T, interchanging C and G, and then reversing the order) of that series of bases (e.g., ATTCGG becomes CCGAAT), calculating a reverse complement of sub-strings from a read-set and/or from sequenced genomic data and/or WGS data may be important when comparing sub-strings from different data sources to look for matching sub-strings. This may eliminate potential redundancy and inaccuracy introduced by the uncertainty of whether a sequence is 3-5 prime or 5-3 prime. If reverse complements are not calculated and included in lists or indexes or sub-strings, then reverse-complement sub-strings that may be indicative of a common species or common organism may evade detection. (In some embodiments, a system could store both a string and its reverse compliment, which may allow look-up to be performed without normalization of query data; however, it could require more space for storage.)

Thus, in some embodiments, when compiling a list, index, or other stored data structure indicating all unique sub-strings associated with a sequence of genomic information, a system may also calculate all reverse complements of all sub-strings in that sequence and may store an indication only of one sub-string of a reverse complement pair of two sub-strings. For example, data representing the string ATTCGG may be stored, while data representing CCGAAT (its reverse complement) may not be additionally stored with reference to the same genetic data. A user or system may select any suitable convention to determine which string of reverse complement pairs is retained and which string is discarded.

Figure 2A:
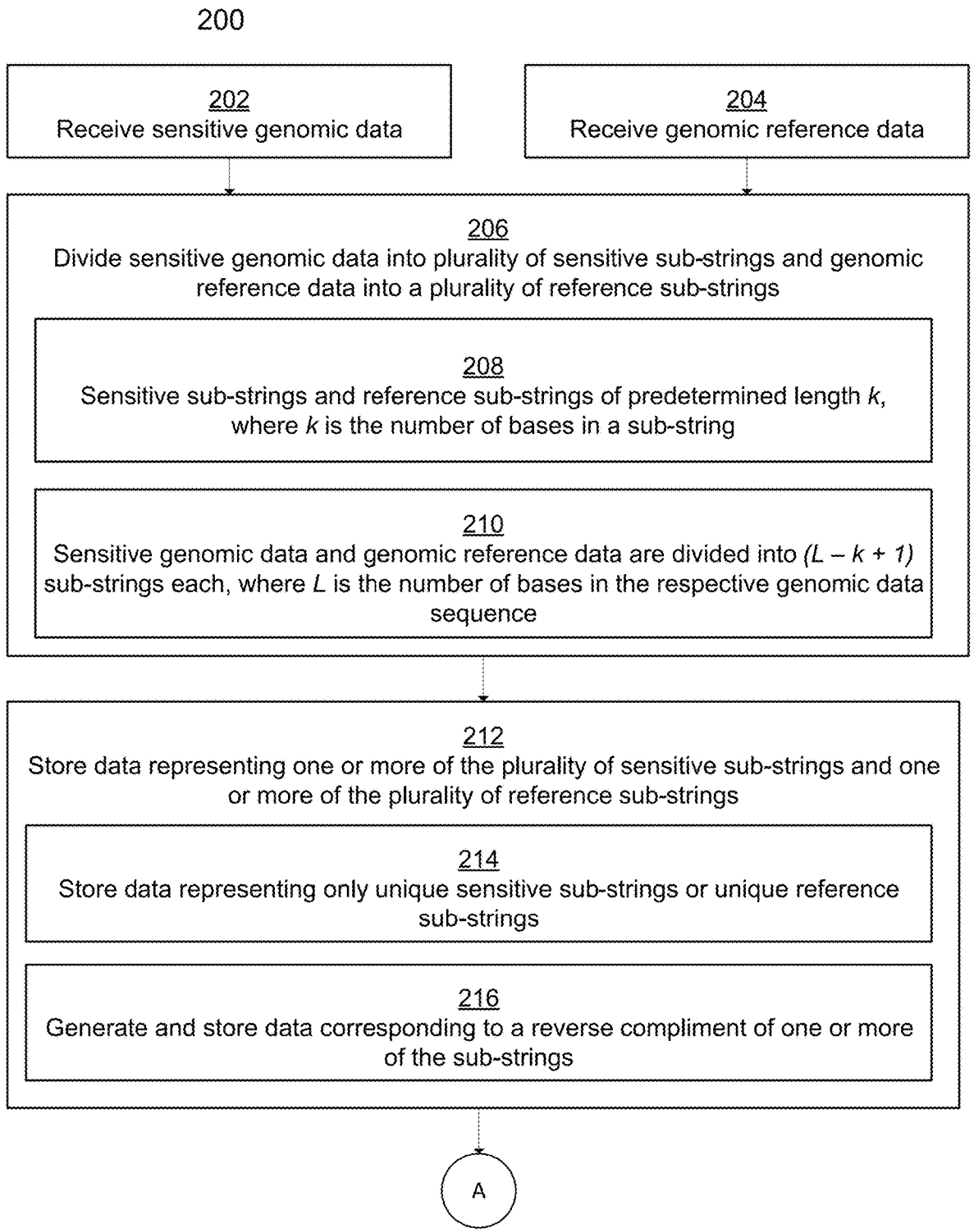
Figure 2B:
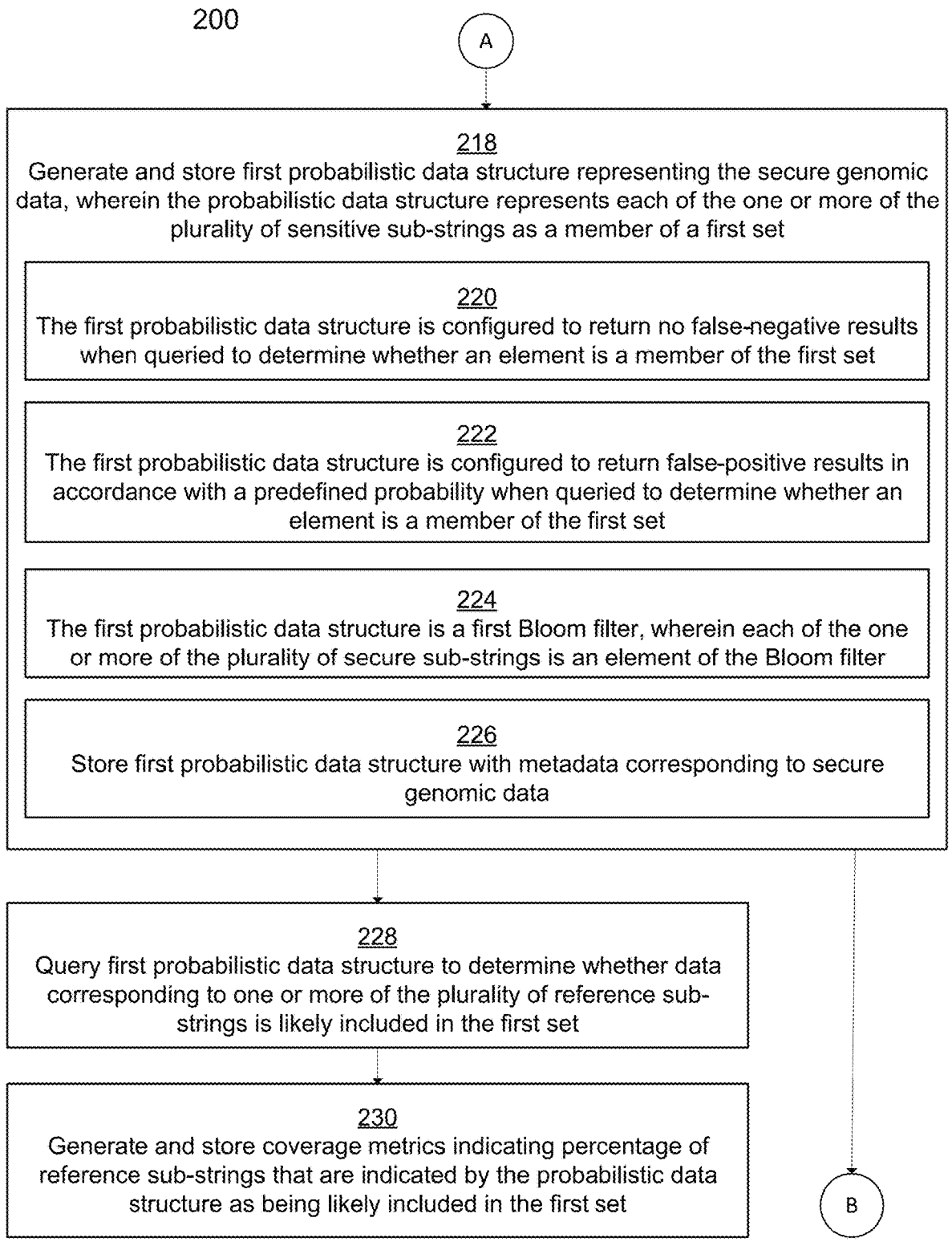

Turning to FIG. 2B, at block 218, in some embodiments, a first probabilistic data structure representing the sensitive genomic data may be generated, wherein the first probabilistic data structure represents each of the one or more of the plurality of sensitive sub-strings as a member of a first set. In some embodiments, after the sensitive genomic data has been divided into sensitive sub-strings, and after data corresponding to one or more of the sensitive sub-strings has been stored, a system may generate a first probabilistic data structure representing each of the one or more sensitive sub-strings. For example, if sensitive genomic data is k-mer-ized and 100 unique sensitive k-mers are identified and stored in association with the sensitive genomic data, then a probabilistic data structure may be generated and stored that represents each of the 100 unique sensitive k-mers as members of a set.

In some embodiments, the probabilistic data structure may be generated by any suitable processor acting on data representing the one or more of the plurality of sensitive sub-strings, and the probabilistic data structure may be built and stored on any suitable computer storage, computer memory, and/or database, or may be transmitted thereto for storage. In the example of system 100 in FIG. 1, genomic information processing computer 130 may generate a probabilistic data structure by performing one or more calculations and operations against stored data representing sensitive sub-strings and may store the probabilistic data structure on encoded genomic information database 140.

In some embodiments, the probabilistic data structure may be configured such that the data elements used to create the probabilistic data structure (e.g., the data upon which the probabilistic data structure was based; the input data used in the creation of the probabilistic data structure) may be unrecoverable from the probabilistic data structure. For example, the probabilistic data structure may comprise a one-way encoding algorithm that prevents the original elements from being recovered based on the probabilistic data structure. In some embodiments, the data elements may be unrecoverable due to an extremely intensive and/or computationally infeasible calculation or calculations that would be required to reverse the encoding and recover the elements. In some embodiments, the data elements may be unrecoverable in that reversal of the encoding may generate additional data elements that were not used in the creation or building of the probabilistic data structure, wherein those additional data elements may be indistinguishable from the data elements on which the probabilistic data structure was actually based; in this way, a party that reverses the encoding process to produce various data elements from the probabilistic data structure may not know which produced data elements were actually used to create the probabilistic data structure and which produced data elements are random, modified, and/or spoof data elements.

At block 220, in some embodiments, the probabilistic data structure may be configured to return no false-negative results when queried to determine whether an element is a member of the first set. At block 222, in some embodiments, the first probabilistic data structure may be configured to return false-positive results in accordance with a predefined probability when queried to determine whether an element is a member of the first set.

In some embodiments, a probabilistic data structure that returns no false-negative results and a predefined and/or user-definable percentage of false positive results may have useful applications in genomic data analytics, in that it may allow for a rapid and effective comparison of known data against the probabilistic data structure to quickly determine, with a known error rate, whether the known data is probably included in the data set or whether the known data is definitely not included in the data set. In some embodiments, such as bioinformatics applications in which large amounts of genomic data may need to be compared to a test sample (e.g., millions of data elements or more), a small error rate in the form of false positive results may be acceptable, in that useful comparative results may still be generated. For example, comparative results may be generated that show a known organism or species with the highest similarity to genomic information of a test sample, and this result may be able to be generated substantially more quickly than if an exhaustive and error-free comparison were made. This is discussed extensively in U.S. Provisional Patent Application No. 62/505,436, filed May 12, 2017, titled "Rapid Genomic Sequence Classification Using Probabilistic Data Structures, ", which is hereby incorporated in its entirety.

Furthermore, in some embodiments, using a probabilistic data structure that returns no false negative results and a predefined and/or user-definable percentage of false positive results may conserve storage space, as the probabilistic data structure may be substantially smaller in size than an exhaustive list or other error-free data structure representing all of the data elements of the set.

In some embodiments, using a probabilistic data structure that returns no false negative results and a predefined and/or user-definable percentage of false positive results may allow for sensitive genomic information to be disclosed safely and without undue risk that an associated party may be determined to be definitively associated with the sensitive genomic information. For example, if a user-definable false positive probability is set to 20%, and the probabilistic data structure then indicates that a reference genomic information compared to the probabilistic data structure is probably a member of the set, then there is still a 20% chance that the reference genomic information being compared to the probabilistic data structure is not actually a member of the set. In this way, while useful, probabilistically hedged information may still be gleaned about potential associations, origins, or other information regarding the sensitive genomic information used to create the probabilistic data structure, parties may be unable to establish with absolute certainty that any specific genomic information is definitively included in the set. Thus, disclosing only a probabilistic data structure with a known false positive error rate may create a mathematical guarantee of plausible deniability that any specific information is actually included in the sensitive information.

In the example of a private organization concerned with being associated with genomic information (e.g., organisms or species) that are known to be associated with an illness or outbreak, then the organization may disclose a probabilistic data structure based on its sensitive and private genomic information (e.g., samples) in order for those data structures to be analyzed, compared, and/or shared along with data from other public and private institutions. However, the private organization may nonetheless be able to avoid an absolute determination that it was associated with the illness or outbreak because it cannot be established with 100% certainty whether any match or association determined is attributable to an actual match or to the false positive characteristics of the probabilistic data structure.

In some embodiments, the false positive probability of the probabilistic data structure may be selectable by a user or a system, such that a false positive probability may be selected and set and used in the creation of the probabilistic data structure. For example, a user may choose to create a probabilistic data structure configured to return false-positive results at any suitable rate, such as 0.1%, 0.5%, 1%, 2%, 5%, 10%, 20%, 25%, 30%, 40%, or 45%. In some embodiments, a probabilistic data structure may be configured to return false positive results at a rate of 50% or more.

In some embodiments, the false positive probability may be selected based at least in part on storage and/or computing resources. For example, the lower the false positive probability, the more storage space may be required to store the probabilistic data structure and the more computational resources may be required to create/build the probabilistic data structure.

In some embodiments, the false positive probability may be selected based at least in part on requirements or considerations for accuracy and precision of comparisons to be made against the probabilistic data structure. For example, in some applications, such as those in which data sets for comparison are smaller, then higher false positive rates may degrade results substantially and unacceptably. However, in some applications, such as those in which data sets for comparison are larger (e.g., hundreds, thousands, or millions of elements to compare), then higher false positive rates may be acceptable as they may not impede the ability to draw meaningful conclusions (e.g., what organism is most likely represented by the k-mers used to build this probabilistic data structure?) from analysis of the probabilistic data structure.

In some embodiments, the false positive probability may be selected based at least in part on considerations regarding data security and/or sensitivity. For example, in some embodiments, if data is indicated as being more secure and/or more sensitive, then a higher false-positive rate may be used, while a lower false-positive rate may be used for data that is indicated as being less secure and/or less sensitive. In some embodiments, an organization seeking to limit potential liability or exposure by creating mathematical uncertainty in the ability to associate the organization with certain genomic information (or other information) used to populate or create a probabilistic data structure may select a predefined false positive probability for the probabilistic data structure in accordance with one or more considerations regarding a level of certainty that would be necessary to impose liability or exposure. For example, if an organization determines that a 30% probability that any indicated result is in fact attributable to a false positive outcome is sufficient to ensure that liability or exposure does not result from the indicated result, then that organization may set the false positive probability of the probabilistic data structure to 30% or more.

At block 224, in some embodiments, the first probabilistic data structure is a Bloom filter, wherein each of the one or more of the plurality of sensitive sub-strings is an element of the Bloom filter. As discussed above, a probabilistic data structure that in some embodiments may provide no false negative results and false positive results at a user-definable predefined probability may be a Bloom filter. In some embodiments, creating the probabilistic data structure may in some embodiments comprise building or creating a Bloom filter, which may be carried out by genomic information processing computer 130 in the example of system 100 of FIG. 1. In some embodiments, a Bloom filter may be created by using each of the plurality of sensitive sub-strings (e.g., the k-mers extracted from the sensitive genomic data) as an element that is used in the creation of the Bloom filter. In some embodiments, a system may be configured to allow for parallel building, exporting and importing from disk, and importing and exporting in several file formats including hex strings of Bloom filters, binary, and reading directly from disk instead of loading into memory. In some embodiments, a system may enable storing statistics about a Bloom filter including the number of elements stored, desired false positive rate, and/or the maximum number of elements to stay below that false positive rate.

At block 226, in some embodiments, the first probabilistic data structure may be stored with metadata corresponding to the sensitive genomic data. For example, the first probabilistic data structure may be stored along with any of the metadata discussed above corresponding to the sensitive genomic data, including any metadata indicating an identity of one or more organisms represented by the data, and/or including any metadata indicating one or more parties associated with the sensitive genomic information. Even in instances in which a private party associated with the sensitive genomic information has reservations or hesitations about being associated with the sensitive genomic information, such a party may nonetheless be willing to disclose identifying metadata along with the probabilistic data structure, and both may be stored (e.g., by system 100 on encoded genomic information database 140) together on one or more computer systems outside the direct control of the private party; the private party may be willing to disclose the probabilistic data structure and associated identifying metadata because of the additional security created by encoding the genomic information such that the genomic information may not be established with absolute certainty on the basis of the probabilistic data structure.

At block 228, in some embodiments, the first probabilistic data structure may be queried to determine whether data corresponding to one or more of the plurality of reference sub-strings is likely included in the first set. In some embodiments, querying the probabilistic data set comprises comparing one or more pieces of information against the probabilistic data set in order to determine whether the piece of information is probably included in the probabilistic data structure or alternately whether it is definitely not included in the probabilistic data structure. In some embodiments, one or more indications may be generated and stored to indicate whether the probabilistic data structure indicates likely inclusion or certain exclusion for any given query.

In some embodiments, when a probabilistic data structure has been created representing contents of sensitive genomic data, the probabilistic data structure may be queried by data associated with genomic reference data. For example, after a probabilistic data structure has been created based on sensitive sub-strings (e.g., k-mers associated with the sensitive genomic data), the probabilistic data structure may then be queried by reference sub-strings (e.g., k-mers associated with the genomic reference data). This query/comparison process may be used to determine whether each of a plurality of reference sub-strings are likely found in the set of sensitive sub-strings that was used to create the probabilistic data structure. In this way, querying the probabilistic data structure built based on a set of sensitive k-mers may be used to determine what reference k-mers are likely also present in the set of sensitive k-mers. If a large number (e.g., a high percentage, such as more than 90%, more than 95% or more than 99%) of reference k-mers associated with a reference genome (e.g., reference data) are found to be likely to be present in the set of sensitive k-mers, then the sensitive genomic information may be determined to be genetically associated with the reference genome, such as being of the same species or the same strain.

At block 230, in some embodiments, coverage metrics may be generated and stored (or transmitted or output) indicating a percentage of reference sub-strings that are indicated by the probabilistic data structure as being likely included in the first set. In some embodiments, a system may compare (e.g., query) each one of a plurality of reference sub-strings associated with a reference organism (e.g., a reference genome) with a probabilistic data structure that was built based on sensitive genomic data. In the example of system 100 of FIG. 1, this comparison/query may be carried out by genomic information processing computer 130.

In some embodiments, calculating coverage metrics such as a number of matching sub-strings and/or a proportion of matching sub-strings may include accounting for sub-strings that appear multiple times in either the original reference nucleic acid sequence or in the original query nucleic acid sequence or query data (e.g., read-set). For example, if a record is stored indicating the number of times that a specific sub-string appeared in an original nucleic acid sequence, then the total number of matching sub-strings indicated by the probabilistic data structure comparison may be multiplied or otherwise weighted in accordance with the stored number of occurrences of the sub-string in the original nucleic acid sequence. In this manner, file size and processing speed may be optimized by not unnecessarily storing duplicate sub-strings, but result data accounting for the strength of coverage and/or matching may be correctly calculated in light of sub-strings that appear multiple times in genomic reference data and/or multiple times in sensitive genomic data.

The system may generate and store an indication of whether the probabilistic data structure indicates likely inclusion or definite exclusion for each one of a plurality of reference sub-strings, and the system may further calculate coverage metrics for the entire plurality of reference sub-strings. For example, the system may calculate a percentage of the reference sub-strings for which the probabilistic data structure indicated likely inclusion, and/or the system may calculate a percentage of the reference sub-strings for which the probabilistic data structure indicated definite exclusion. These and other coverage metrics may be generated and stored in any suitable computer storage, such as in encoded genomic information database 140. The coverage metrics also may be transmitted to one or more other systems, including transmission to parties associated with the sensitive genomic data and/or to third parties.

In some embodiments, the system may generate, store, and/or transmit one or more indications of a likely identification and/or match for the sensitive genomic data. For example, a system may query the probabilistic data structure associated with the sensitive genomic data by a plurality of sets of reference sub-strings associated with various known/identified organisms and may calculate a percentage of matching sub-strings for the set associated with each known/identified organism. The system may then output an indication of the organisms with the highest percentage of matching sub-strings and may rank the organisms according to percentage. By looking at the highest-ranked organisms, a user of the system may glean a prediction as to an identification/identity of one or more organisms associated with the sensitive genomic data used to create the probabilistic data structure.

Turning to FIG. 2C, in some embodiments, block 232 may follow from blocks 218-226. At block 232, in some embodiments, a second probabilistic data structure representing the genomic reference data may be generated, wherein the probabilistic data structure represents each of the one or more of the plurality of reference sub-strings as a member of a second set. The second probabilistic data structure may share some or all of the characteristics of the first probabilistic data structure as discussed above and may be created and/or processed in some or all of the same ways. In some embodiments, a predefined false positive probability may be the same for the first and second probabilistic data structures, while in some embodiments it may be different. In some embodiments, the second probabilistic data structure may be stored in any of the same or similar locations, including being stored in any of the same or similar databases, as discussed above with respect to the first probabilistic data structure. In some embodiments, the second probabilistic data structure may be stored in association with metadata (which may be the same or similar to any of the metadata discussed above with reference to the first probabilistic data structure) such as any metadata identifying or otherwise associated with an identity, associated party, or any other property of the reference genomic information used to create the second probabilistic data structure. In some embodiments, a system may store a plurality of probabilistic data structures each representing different reference genomic data associated with respective reference genomes.

At block 234, in some embodiments, the second probabilistic data structure is a second Bloom filter, wherein each of the one or more of the plurality of sub-strings is an element of the Bloom filter. The second probabilistic data structure may differ from the first probabilistic data structure chiefly in that the second probabilistic data structure may be built/generated based on sub-strings (e.g., k-mers) of the genomic reference data, rather than being built based on sub-strings (e.g., k-mers) of the sensitive genomic data.

At block 236, in some embodiments, the first probabilistic data structure may be compared to the second probabilistic data structure. In some embodiments, rather than comparing the first probabilistic data structure to a plurality of reference sub-strings on an individual, one-at-a-time basis as discussed above, a direct comparison of two probabilistic data structures may be made. In the example of system 100 of FIG. 1, genomic information processing computer 140 may compare two or more probabilistic data structures, such as two or more probabilistic data structures stored on encoded genomic information database 140, to one another.

In some embodiments, two or more probabilistic data structures may be compared by treating each probabilistic data structure as a sets and calculating the union, intersection, and difference between them. The result may be a new probabilistic data structure containing the information set based on the calculation performed. Union and intersection may be used to find what two samples have in common (intersection).

At block 238, in some embodiments, based on the comparison of the first probabilistic data structure and the second probabilistic data structure, an index indicative of a similarity of the first probabilistic data structure and the second probabilistic data structure may be generated and stored (or transmitted or output). In some embodiments, the index may be stored on encoded genomic information database 140 of system 100 or may be stored on or transmitted to any other associated computer system or storage system. In some embodiments, the index may be stored along with metadata regarding one or both of the probabilistic data structures (such as any of the metadata discussed above) and/or regarding the comparison of the probabilistic data structures (e.g., time, place, and/or method of comparison; identity of probabilistic data structures; etc.).

At block 240, in some embodiments, the index is a Jaccard index indicating a similarity of the first and second Bloom filters. In some embodiments in which the first and second probabilistic data structures are Bloom filters, the Bloom filters may be compared with one another to generate a Jaccard index, which may be a number between zero and one. In some embodiments, a number closer to zero may indicate more dissimilarity, while a number closer to one may indicate more similarity. In some embodiments, a system or a user may determine, in accordance with the value generated for the Jaccard index, whether genomic information represented by the first probabilistic data structure likely does or does not correspond to a same organisms, species, and/or strain as genomic information represented by the second probabilistic data structure. In some embodiments, probabilistic thresholds for a Jaccard index value (or for an index value in general, for the case of probabilistic data structures other than Bloom filters, or the case of other methods of comparing Bloom filters) may be determined and applied. For example, one or more thresholds may be applied to determine whether two probabilistic data structures likely represent the same organism, species, and/or strain, where a Jaccard index value above a predefined threshold may indicate matching and a Jaccard index value below a predefined threshold may indicate a the absence of a match.

Although the description herein uses terms first, second, etc. to describe various elements, these elements should not be limited by the terms. These terms are only used to distinguish one element from another.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

What is claimed is:

1. A system for securely communicating genomic information from a secure computing environment to an unsecure computing environment, the system comprising:
   one or more hardware processors located in the secure computing environment;
   a memory located in the secure computing environment, the memory storing one or more programs, the one or more programs configured to be executed by the one or more hardware processors and including instructions to:
   receive data representing a nucleic acid sequence;
   receive data indicating a security level associated with the received data representing a nucleic acid sequence;
   divide the data into a plurality of portions, wherein each of the plurality of portions represents a sub-string of the nucleic acid sequence;
   store data, in the secure computing environment, representing one or more of the plurality of portions;
   encode the data representing the nucleic acid sequence by generating, based on the data representing one or more of the plurality of portions, data including a probabilistic data structure that represents each of the one or more of the plurality of portions as members of a set, wherein generating the probabilistic data structure comprises setting a pre-defined false-positive probability of the probabilistic data structure, and wherein the false-positive probability is set at least in part based on the indicated security level of the data representing the nucleic acid sequence;
   transmit the encoded nucleic acid sequence, including the probabilistic data structure, for storage in the unsecure computing environment, in association with metadata corresponding to the data representing the nucleic acid sequence.

2. The system of claim 1, wherein the probabilistic data structure is configured to be queried by an element, and to responsively generate data indicating whether the element is a member of the set.

3. The system of claim 1, wherein generating data indicating whether the element is a member of the set comprises one of generating data indicating that the element is definitely not a member of the set and generating data indicating that the element is probably a member of the set.

4. The system of claim 1, wherein the predefined false-positive probability is set at least in part in accordance with a target file size for the probabilistic data structure.

5. The system of claim 1, wherein the predefined false-positive probability is set at least in part in accordance with available storage resources.

6. The system of claim 1, wherein the predefined false-positive probability is set at least in part in accordance with available processing resources.

7. The system of claim 1, wherein the predefined false-positive probability is set at least in part in accordance with requirements for accuracy of comparisons to be made against the probabilistic data structure.

8. The system of claim 1, wherein the predefined false-positive probability is set at least in part in accordance with a level of sensitivity of the data representing a nucleic acid sequence.

9. A method for storing one or more programs for securely communicating genomic information from a secure computing environment to an unsecure computing environment, the method comprising:
   at a system comprising one or more processors located in the secure computing environment and a memory located in the secure computing environment:
   receiving data representing a nucleic acid sequence;
   receiving data indicating a security level associated with the received data representing a nucleic acid sequence;
   dividing the data into a plurality of portions, wherein each of the plurality of portions represents a sub-string of the nucleic acid sequence;
   storing data, in the secure computing environment, representing one or more of the plurality of portions;
   encoding the data representing the nucleic acid sequence by generating, based on the data representing one or more of the plurality of portions, data including a probabilistic data structure that represents each of the one or more of the plurality of portions as members of a set, wherein generating the probabilistic data structure comprises setting a pre-defined false-positive probability of the probabilistic data structure, and wherein the false-positive probability is set at least in part based on the indicated security level of the data representing the nucleic acid sequence;
   transmitting the encoded nucleic acid sequence, including the probabilistic data structure, for storage in the unsecure computing environment, in association with metadata corresponding to the data representing the nucleic acid sequence.

10. A non-transitory computer-readable storage medium storing one or more programs for securely communicating genomic information from a secure computing environment to an unsecure computing environment, the one or more programs configured to be executed by one or more processors located in the secure computing environment, the one or more programs including instructions to:
   receive data representing a nucleic acid sequence;
   receive data indicating a security level associated with the received data representing a nucleic acid sequence;
   divide the data into a plurality of portions, wherein each of the plurality of portions represents a sub-string of the nucleic acid sequence;
   store data, in the secure computing environment, representing one or more of the plurality of portions;
   encode the data representing the nucleic acid sequence by generating, based on the data representing one or more of the plurality of portions, data including a probabilistic data structure that represents each of the one or more of the plurality of portions as members of a set, wherein generating the probabilistic data structure comprises setting a pre-defined false-positive probability of the probabilistic data structure, and wherein the false-positive probability is set at least in part based on the indicated security level of the data representing the nucleic acid sequence;
   transmit the encoded nucleic acid sequence, including the probabilistic data structure, for storage in the unsecure computing environment, in association with metadata corresponding to the data representing the nucleic acid sequence.

11. A system for securely comparing genomic information in an unsecure computing environment, the system comprising:
   one or more hardware processors located in the unsecure computing environment;
   a memory located in the unsecure computing environment, the memory storing one or more programs, the one or more programs configured to be executed by the one or more hardware processors and including instructions to:
   receive, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence;
   receive, from the first source, first metadata associating the encoded data with the first source;
   receive, from a second source, data representing a reference nucleic acid sequence and associated second metadata that identifies an organism associated with the reference nucleic acid sequence;
   extract, from the data representing the reference nucleic acid sequence, a plurality of sub-strings each representing a portion of the reference nucleic acid sequence;
   query the probabilistic data structure by each of the plurality of sub-strings extracted from the reference nucleic acid sequence;
   generate, in response to the querying, result data comprising one or more indications of whether each of the plurality of sub-strings extracted from the reference nucleic acid sequence is a member of the set of sub-strings of the first nucleic acid sequence;
   determine, based on the result data, whether the first nucleic acid sequence corresponds to the organism associated with the reference nucleic acid sequence, wherein the determining comprises determining, when more than a predefined threshold of the plurality of sub-strings extracted from the reference nucleic acid sequence are indicated by the result data as being members of the set of sub-strings of the first nucleic acid sequence, that the first nucleic acid sequence corresponds to the organism associated with the reference nucleic acid sequence; and store the result data in association with one or more of the first and second metadata.

12. A method for securely comparing genomic information in an unsecure computing environment, the method comprising:

at a system comprising one or more processors located in the unsecure computing environment and a memory located in the unsecure computing environment:

receiving, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence;

receiving, from the first source, first metadata associating the encoded data with the first source;

receiving, from a second source, data representing a reference nucleic acid sequence and associated second metadata that identifies an organism associated with the reference nucleic acid sequence;

extracting, from the data representing the reference nucleic acid sequence, a plurality of sub-strings each representing a portion of the reference nucleic acid sequence;

querying the probabilistic data structure by each of the plurality of sub-strings extracted from the reference nucleic acid sequence;

generating, in response to the querying, result data comprising one or more indications of whether each of the plurality of sub-strings extracted from the reference nucleic acid sequence is a member of the set of sub-strings of the first nucleic acid sequence;

determining, based on the result data, whether the first nucleic acid sequence corresponds to the organism associated with the reference nucleic acid sequence, wherein the determining comprises determining, when more than a predefined threshold of the plurality of sub-strings extracted from the reference nucleic acid sequence are indicated by the result data as being members of the set of sub-strings of the first nucleic acid sequence, that the first nucleic acid sequence corresponds to the organism associated with the reference nucleic acid sequence; and storing the result data in association with one or more of the first and second metadata.

13. A non-transitory computer-readable storage medium storing one or more programs for securely comparing genomic information in an unsecure computing environment, the one or more programs configured to be executed by one or more processors and including instructions to:

receive, from a first source located in a secure computing environment, encoded data representing a first nucleic acid sequence, the encoded data comprising a probabilistic data structure that represents a plurality of elements as members of a set, wherein each of the plurality of elements corresponds to a nucleic acid sub-string of a the first nucleic acid sequence;

receive, from the first source, first metadata associating the encoded data with the first source;

receive, from a second source, data representing a reference nucleic acid sequence and associated second metadata that identifies an organism associated with the reference nucleic acid sequence;

extract, from the data representing the reference nucleic acid sequence, a plurality of sub-strings each representing a portion of the reference nucleic acid sequence;

query the probabilistic data structure by each of the plurality of sub-strings extracted from the reference nucleic acid sequence;

generate, in response to the querying, result data comprising one or more indications of whether each of the plurality of sub-strings extracted from the reference nucleic acid sequence is a member of the set of sub-strings of the first nucleic acid sequence;

determine, based on the result data, whether the first nucleic acid sequence corresponds to the organism associated with the reference nucleic acid sequence, wherein the determining comprises determining, when more than a predefined threshold of the plurality of sub-strings extracted from the reference nucleic acid sequence are indicated by the result data as being members of the set of sub-strings of the first nucleic acid sequence, that the first nucleic acid sequence corresponds to the organism associated with the reference nucleic acid sequence; and store the result data in association with one or more of the first and second metadata.

\* \* \* \* \*